United States Patent [19]

Douglas

[11] Patent Number: 5,310,546
[45] Date of Patent: * May 10, 1994

[54] MOUTHRINSE AND METHOD OF PREPARATION

[75] Inventor: Jerry A. Douglas, Harrisburg, Ill.

[73] Assignee: 7-L Corporation, Harrisburg, Ill.

[*] Notice: The portion of the term of this patent subsequent to Dec. 29, 2009 has been disclaimed.

[21] Appl. No.: 327,199

[22] Filed: Dec. 24, 1992

Related U.S. Application Data

[63] Continuation of Ser. No. 755,149, Sep. 5, 1991, Pat. No. 5,174,990, which is a continuation-in-part of Ser. No. 603,570, Oct. 25, 1990, Pat. No. 5,104,644, which is a continuation-in-part of Ser. No. 476,153, Feb. 7, 1990, abandoned.

[51] Int. Cl.$^5$ .......................... A61K 7/16; A61K 7/20; A61K 33/40
[52] U.S. Cl. ..................... 424/53; 424/616; 424/641; 424/642
[58] Field of Search .................. 424/49–58, 424/616, 641, 642

[56] References Cited

U.S. PATENT DOCUMENTS

| | | |
|---|---|---|
| 1,275,275 | 8/1918 | Levinson . |
| 2,556,567 | 6/1951 | Wright . |
| 3,887,704 | 6/1975 | Lichtenstein ................. 424/145 |
| 3,947,570 | 3/1976 | Pensak et al. ................. 424/54 |
| 4,022,880 | 5/1977 | Vinson et al. ................. 424/49 |
| 4,100,269 | 7/1978 | Pader . |
| 4,150,151 | 4/1979 | Pader et al. ................. 424/56 |
| 4,160,821 | 7/1979 | Sipos ................. 424/49 |
| 4,226,851 | 10/1980 | Sompayrac . |
| 4,339,432 | 7/1982 | Ritchey et al. . |
| 4,395,398 | 7/1983 | Yamamoto . |
| 4,406,882 | 9/1983 | Turner ................. 424/49 |
| 4,420,471 | 12/1983 | Elton et al. ................. 424/49 |
| 4,425,325 | 1/1984 | Ritchey et al. . |
| 4,477,438 | 10/1984 | Wilcockson . |
| 4,522,806 | 6/1985 | Muhlemann et al. . |
| 4,537,778 | 8/1985 | Clipper et al. . |
| 4,550,018 | 10/1985 | Ambike et al. ................. 424/52 |
| 4,568,540 | 2/1986 | Asano et al. . |
| 4,647,452 | 3/1987 | Ritchey et al. . |
| 4,684,517 | 8/1987 | Clipper et al. . |
| 4,895,727 | 1/1990 | Allen . |
| 4,937,066 | 6/1990 | Vlock . |
| 4,961,923 | 10/1990 | Heyde . |
| 4,980,152 | 12/1990 | Frazier et al. . |
| 4,992,259 | 2/1991 | Schiraldi et al. . |
| 5,035,882 | 7/1991 | Hussein et al. ................. 424/58 |
| 5,104,644 | 4/1992 | Douglas ................. 424/53 |
| 5,174,990 | 12/1992 | Douglas ................. 424/53 |

FOREIGN PATENT DOCUMENTS

91/11987 8/1991 PCT Int'l Appl. .
93/04664 4/1993 PCT Int'l Appl. .

*Primary Examiner*—Shep K. Rose
*Attorney, Agent, or Firm*—Senniger, Powers, Leavitt & Roedel

[57] ABSTRACT

A mouthrinse preparation having between about 0.25% and about 0.65% hydrogen peroxide, between about 0.005% and about 0.1% zinc chloride, at least about 0.012% sodium citrate, at least about 0.03% sodium lauryl sulfate at least about 0.006% citric acid and ethanol in an amount less than about 3%, the mouthrinse preparation remaining stable upon continuous exposure to a temperature of 37° C. at atmospheric pressure for at least 30 days. A method for preparation of same.

17 Claims, 9 Drawing Sheets

Fig. 4 Effect of Prevention Mouthrinse on S. mutans : Bactericidal Kinetics

Fig. 5  Effect of Prevention Mouthrinse on S. milleri : Bactericidal Kinetics

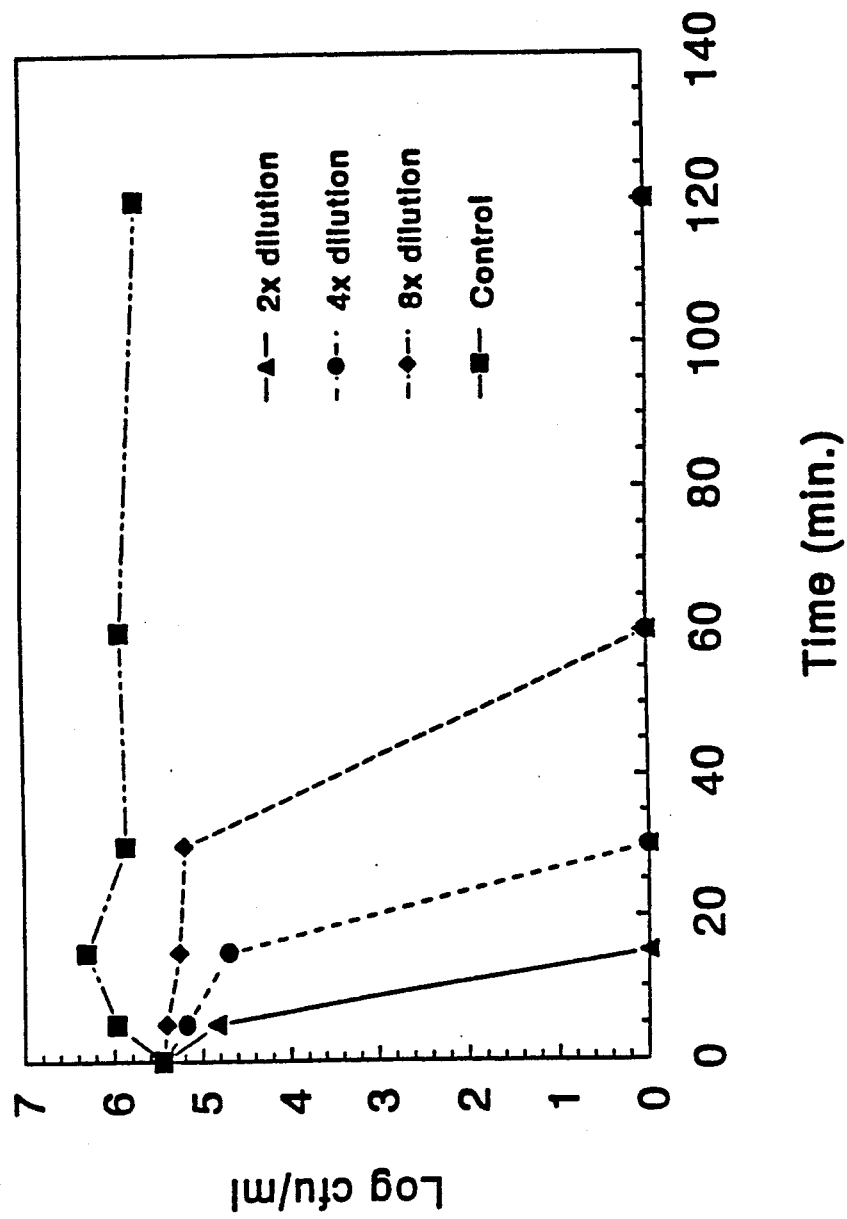
Fig. 7  Effect of Prevention Mouthrinse on C. albicans : Fungicidal Kinetics

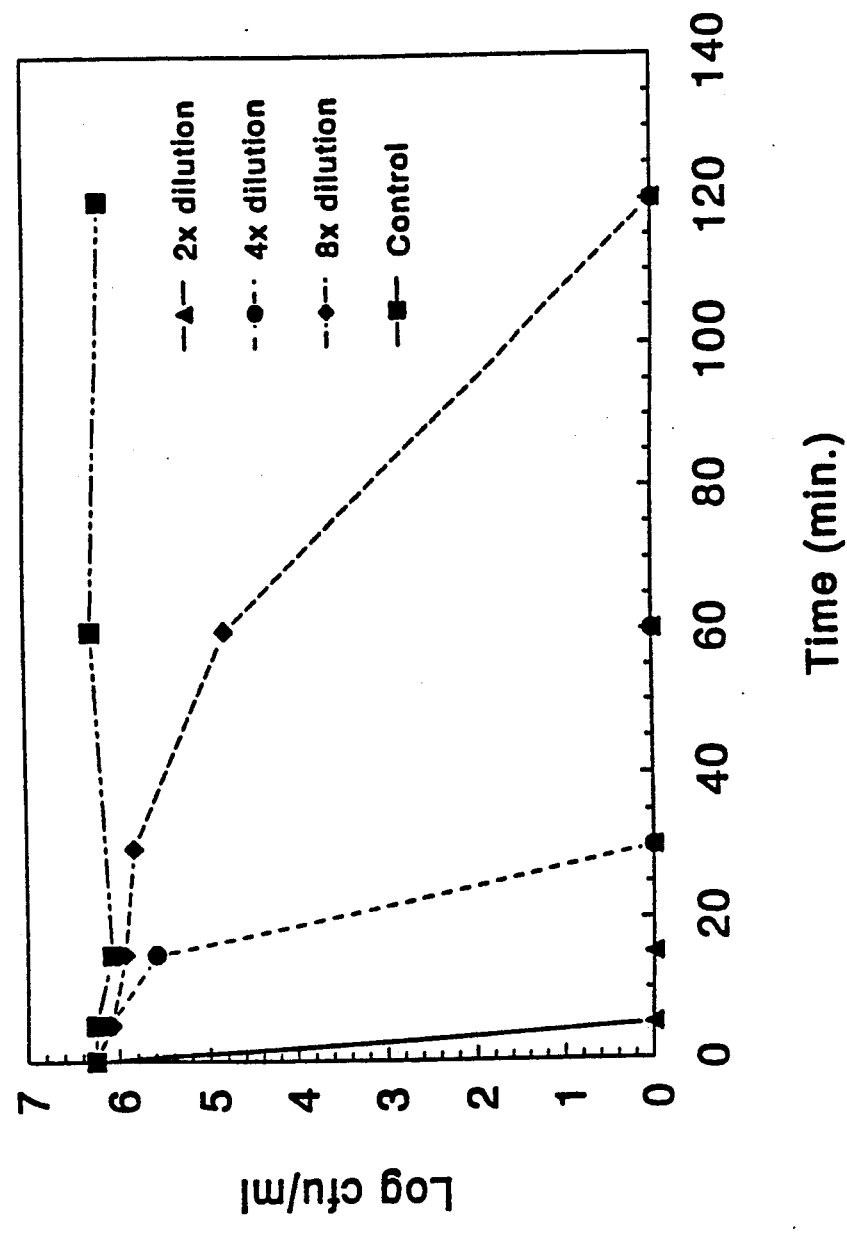
Fig. 8 Effect of Prevention Mouthrinse on A. viscosus : Bactericidal Kinetics

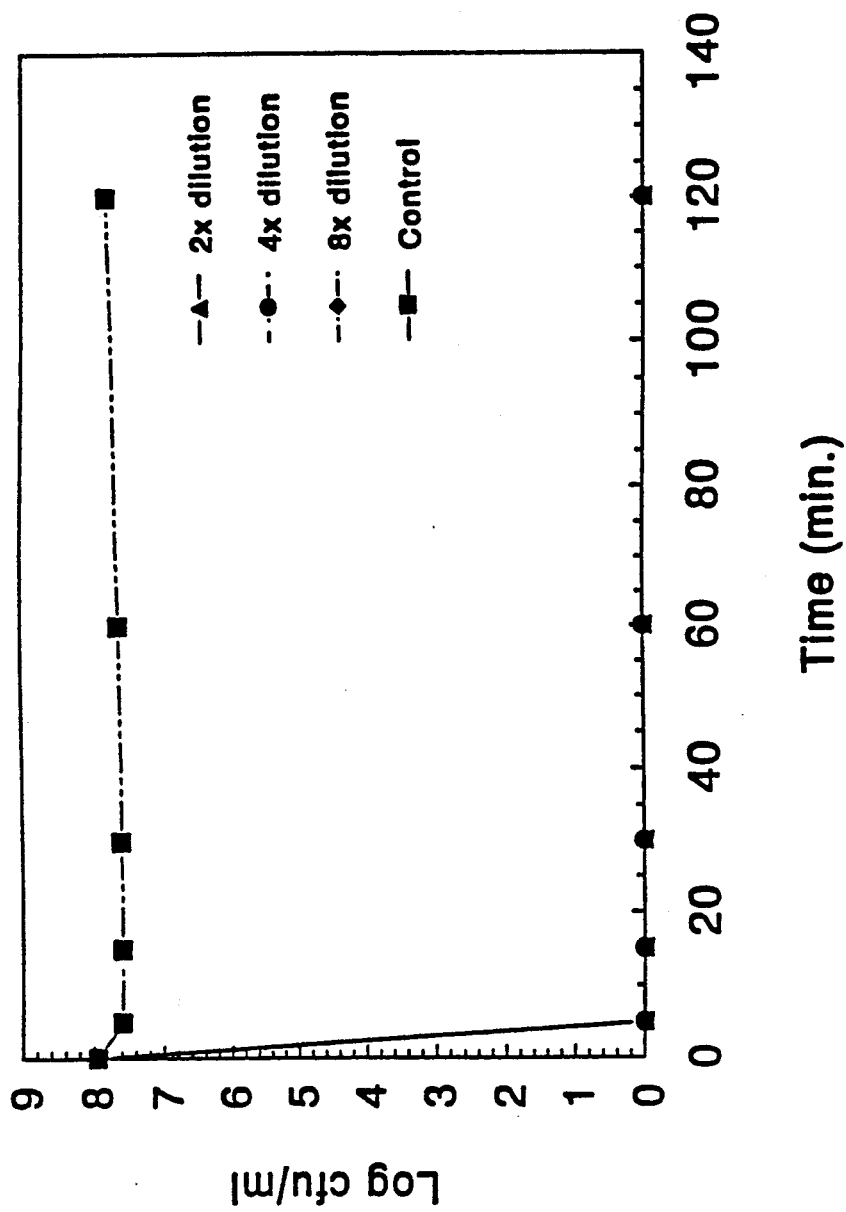
Fig. 9 Effect of Prevention Mouthrinse on *A. actinom.* : Bactericidal Kinetics

MOUTHRINSE AND METHOD OF PREPARATION

This is a continuation of application Ser. No. 07/755,149, filed Sep. 5, 1991, now U.S. Pat. No. 5,174,990, which is a continuation-in-part of application Ser. No. 07/603,570, filed Oct. 25, 1990, now U.S. Pat. No. 5,104,644, which is a continuation-in-part of application Ser. No. 07/476,153, filed Feb. 7, 1990, now abandoned.

BACKGROUND OF THE INVENTION

This invention is directed to a mouthrinse preparation for the purposes of oral therapy and the prevention of dental disease. More particularly, the invention is directed to a chemically stable mouthrinse composition which includes hydrogen peroxide and a method for preparation of such a mouthrinse.

Hydrogen peroxide and peroxide-containing preparations are known to be effective therapeutic and prophylactic treatments for caries, periodontal hemorraging, plaque, gingivitis, periodontitis, orthodontic appliance damage and other oral conditions. Frazier et al., U.S. Pat. No. 4,980,152, disclose an oral preparation containing between 0.5% and 10% hydrogen peroxide.

Mouthrinses are known to contain numerous adjuvants in addition to hydrogen peroxide. Schiraldi et al., U.S. Pat. No. 4,992,259, disclose the use of zinc compounds including zinc chloride as astringent-desensitizing agents.

Additionally, flavorings and colorings have been added to mouthrinses to improve their acceptability to the user. Surfactants have been added to enhance the bacterial activity of the mouthrinse. Anticoagulants have also been included to help the healing of hemorragic tissue.

Oral preparations containing such other ingredients in conjunction with hydrogen peroxide, however, have generally been unstable in storage, as the hydrogen peroxide reacts with one or more of the other ingredients in the preparation and components of the mouthrinse tend to precipitate. As a result, the capacity of the hydrogen peroxide to release oxygen and of the other ingredients to perform their respective functions is lost or greatly diminished even after relatively short storage periods as, for example, on a drug store display shelf. Additionally, the instability of mouthrinses containing hydrogen peroxide has been known to render them unsatisfactory with respect to shelf-life requirements of the United States Food and Drug Administration.

Oral preparations also often contain relatively high concentrations of various alcohols for their effects of sterilizing, transporting and stabilizing. Asano et al., U.S. Pat. No. 4,568,540, disclose oral preparations having at least 35% sorbitol. Commercially available mouthrinses often contain between about 15% and 30% alcohol.

Recently there has been increasing concern about the high alcohol content of commercially available mouthrinses. Scientific studies have linked the regular use of such mouthrinses to significant increases in the incidence of oral cancer. Additionally, there is a risk that alcoholic persons may intentionally ingest high alcohol mouthrinses, that children may incur serious injuries due to poisoning from high alcohol mouthrinses, and that adolescents may abuse such mouthrinses where liquor laws otherwise render alcohol unobtainable.

SUMMARY OF THE INVENTION

Accordingly, it is an object of this invention to provide a chemically stable mouthrinse containing an amount of hydrogen peroxide which is effective for therapeutic and preventative oral treatment; it is a further object to provide a chemically stable mouthrinse containing an effective amount of hydrogen peroxide and having an acceptable taste and color; to provide a chemically stable mouthrinse which contains an effective amount of hydrogen peroxide and meets United States Food and Drug Administration requirements regarding shelf life; to provide a chemically stable mouthrinse containing an effective amount of hydrogen peroxide and at least one additional antimicrobial agent; to provide a chemically stable mouthrinse containing an effective amount of hydrogen peroxide and a surfactant; to provide a chemically stable mouthrinse containing an effective amount of hydrogen peroxide and an anticoagulant; to provide a mouthrinse which has a low alcohol content.

Briefly, therefore, the present invention is directed to a mouthrinse preparation having between about 0.25% and about 0.65% hydrogen peroxide, between about 0.005% and about 0.1% zinc chloride, a t least about 0.012% sodium citrate, the sodium citrate content being such that the ratio of sodium citrate to zinc chloride is in the range of from about I to 1 to about 2 to 1, at least about 0.03% sodium lauryl sulfate, the sodium lauryl sulfate content being such that the ratio of sodium lauryl sulfate to zinc chloride is in the range of from about 2 to 1 to about 8 to 1, at least about 0.006% citric acid and between about 2% and about 3.5% ethanol, said mouthrinse preparation having an acceptable shelf life.

The invention is also directed to a method for preparing a mouthrinse preparation involving the steps of providing a solution containing alcohol, preparing a zinc chloride solution by dissolving zinc chloride in deionized water and allowing the zinc chloride solution to cool, adding sodium lauryl sulfate, citric acid and sodium citrate to the zinc chloride solution, mixing the zinc chloride solution and allowing it to cool, mixing the alcohol solution with the zinc chloride solution and allowing a resulting solution to cool, and adding a hydrogen peroxide solution to the resulting solution and mixing to provide a mouthrinse.

DETAILED DESCRIPTION

The present invention is directed to a mouthrinse composition for the purposes of oral therapy and the prevention of dental disease. More particularly, the invention is directed to a chemically stable mouthrinse composition which includes hydrogen peroxide. The invention is also directed to a method for the preparation of such a mouthrinse.

The mouthrinse composition of the present invention comprises an oxygen-releasing agent which also acts as an astringent and anti-inflammatory agent, specifically, hydrogen peroxide. Hydrogen peroxide helps prevent the accumulation and multiplication in the mouth of anaerobic bacteria generally associated with periodontal complications. The hydrogen peroxide has both a chemical effect as oxygen contacts the microbiota and a mechanical effect as the bubbling and foaming action of the peroxide upon swishing contact with saliva and oral tissue facilitates the delivery of active ingredients to affected areas. This chemical/mechanical action also facilitates the cleansing removal of microbiota, plaque, inflamed tissue and other local factors. Preferably, the mouthrinse comprises between about 0.25% and about 0.65% hydrogen peroxide (all percentages herein are on a weight/volume basis unless indicated otherwise). Hydrogen peroxide in amounts significantly less than about 0.25% would be insufficient to provide the desired therapeutic effect, whereas amounts significantly greater than about 0.65% would be potentially unstable under conditions of prolonged storage.

Zinc chloride is provided in the mouthrinse as an antimicrobial agent having an antiplaque effect. Zinc chloride advantageously has the ability to interfere with the metabolic activity of pathogenic microbiota. Zinc chloride helps reduce gingival inflammation and restore edematous tissue to its normal state. The mouthrinse preferably comprises between about 0.005% and about 0.1% zinc chloride. Zinc chloride in amounts significantly less than about 0.005% would be insufficient to provide the desired therapeutic effect. A zinc chloride composition significantly greater than about 0.1% would make the mouthrinse unacceptably bitter in taste to be suitable for most normal human treatments. A significantly greater than normal microbiota population in the mouth of the host may indicate, or an unusually high tolerance for bitter taste may permit, the use of zinc chloride in amounts greater than about 0.1%.

The mouthrinse comprises sodium lauryl sulfate as a surfactant. Without being bound to any theory, it is believed that sodium lauryl sulfate serves to enhance the interaction among the mouthrinse, saliva and oral tissue. Additionally, sodium lauryl sulfate makes the cell walls of the microbiota more permeable, interferes with the metabolic processes of the microbiota, and enhances the ability of zinc chloride to interfere with the metabolic processes of the microbiota. The preferred mouthrinse composition comprises at least about 0.03% sodium lauryl sulfate. Although there is no critical maximum for sodium lauryl sulfate content, it is preferred to be provided in an amount such that the ratio of sodium lauryl sulfate to zinc chloride is in the range of from about 2 to 1 to about 8 to 1, most preferably about 4 to 1.

An anticoagulant to aid in the healing of hemorragic tissue is also provided in the mouthrinse. The preferred anticoagulant is sodium citrate, which also serves as an antimicrobial enhancer and an anti-inflammatory agent. Sodium citrate is provided in an amount of at least about 0.012% and up to about 0.2% or greater. It is preferred that sodium citrate is provided in an amount such that the ratio of sodium citrate to zinc chloride is from about 1 to 1 to about 2 to 1.

Citric acid is provided in the mouthrinse for purposes of demineralization and stabilization. Citric acid is effective for adjusting and maintaining the pH of the mouthrinse in a range at which the hydrogen peroxide remains stable, roughly from about 3.5 to about 4.5. The citric acid content, which is substantially always greater than about 0.005%, is therefore that amount which is effective for achievement of the desired pH.

Any of a variety of pharmaceutically acceptable carrier media may be used including an aqueous alcohol. The presence of alcohol in the carrier provides sterilization capacity and is thought to influence product stability. The preferred carrier contains the denatured alcohol SD alcohol 38 B-2, which contains about 92% ethyl alcohol. It being an object of this invention to provide a low alcohol mouthrinse, it is preferred that the mouthrinse contain less than about 5% alcohol (mouthrinse total R-OH content) and, most preferably, less than about 3% alcohol.

The alcohol may be denatured with any of a variety of denaturing agents, alone or in combination, including, nonexclusively, anethole, anise oil, bay oil, bergamot oil, bitter almond oil, bubble-gum flavoring, cedar leaf oil, cinnamic aldehyde, cinnamon oil, clove oil, eucalyptol, eucalyptus oil, eugenol, lavender oil, menthol, peppermint oil, sassafras oil, spearmint oil, terpeneless spearmint oil, thyme oil, thymol and/or wintergreen oil. Generally, less than about 0.1% total denaturing agent is preferred in the mouthrinse. The preferred alcohol also contains poloxamer 407 or another solubilizer to solubilize the denaturing agents. Generally, less than about 1.0 wt. % poloxamer 407 is preferred.

In addition to the above-described components, the mouthrinse of the present invention may also contain glycerin, which is believed to serve as an additional surfactant. Glycerin may be present in the range of from about 1.8% to about 9.0%.

The mouthrinse may also contain an appropriate chelating agent to keep the various minerals in combination. The preferred chelating agent is disodium EDTA provided in the range of from about 0.022% to about 0.1%.

Any of a number of pharmaceutically safe and compatible coloring agents, including, nonexclusively, D & C yellow #10 and D & C green #3, may also be used in effective amounts to enhance the acceptability of the mouthrinse.

The mouthrinse of the invention may optionally contain any of a variety of sweetening agents alone or in combination. Sweetening agents may include, for example, saccharin, dextrose, levulose, and/or aspartame. Although the sweetening agent content of the mouthrinse is variably dependent on the taste sought to be imparted and the strength of the selected sweetener, it is generally preferred that the sweetening agent content be less than about 2.5%.

In accordance with the method of the invention, the particular constituents of the mouthrinse, in quantities as described hereinabove, are mixed in the following manner. A 1% hydrogen peroxide solution is provided. This can be prepared by diluting a 3% hydrogen peroxide solution with deionized water to a strength of about 1%.

An alcohol solution comprising ethanol, denaturing agents and a solubilizer is provided. This alcohol solution may be prepared by mixing its components until clear or may be obtained from any of numerous commercial suppliers.

A zinc chloride solution is prepared by dissolving the zinc chloride in deionized water and mixing until the solution is clear. To achieve a mouthrinse having stabilized hydrogen peroxide, the heat generated from this mixing process is allowed to dissipate prior to further processing of this zinc chloride solution.

A solution of remaining ingredients is prepared by dissolving the remaining mouthrinse components in deionized water. In the preferred embodiment, these components include sodium lauryl sulfate, citric acid, sodium citrate, glycerin, disodium EDTA, saccharin and the selected coloring agents.

The remaining ingredient solution is then mixed with the zinc chloride solution. The heat generated from the mixing process is allowed to dissipate prior to further processing.

As an alternative to preparing the above-described remaining ingredient solution and subsequently mixing it with the zinc chloride solution, these components may optionally be added directly to, and mixed with, the cooled zinc chloride solution. To achieve a mouthrinse having stabilized hydrogen peroxide, the heat generated from the mixing process is allowed to dissipate prior to further processing.

The alcohol solution is mixed with the solution comprising the zinc chloride and the remaining ingredients until it is substantially clear, except for the effect of any coloring agents present. To achieve a mouthrinse having stabilized hydrogen peroxide, the heat generated from this mixing process is allowed to dissipate prior to further processing.

The 1% hydrogen peroxide solution is then mixed with the solution comprising the zinc chloride, alcohol and remaining ingredients to provide the mouthrinse of the invention.

Mouthrinses prepared in accordance with the method of this invention are characterized by superior chemical stability and, consequently, shelf life. The mouthrinses are thus stable, i.e., they remain clear, with no visible formation of precipitates or detectable evolution of gases after prolonged periods of storage, i.e., 30, 60, and 90 days of continuous exposure to temperatures of 37° C. and atmospheric pressure.

The following examples illustrate the invention.

EXAMPLE 1

About 0.83 gallons of a 3% hydrogen peroxide solution was diluted with about 1.66 gallons of deionized water to provide a 1% hydrogen peroxide solution.

About 0.24 gallons of SD alcohol 38 B-2 comprising peppermint oil and spearmint oil denaturing agents, poloxamer 407 stabilizer, and about 92% ethyl alcohol was mixed with deionized water to a total volume of about 3.5 gallons and provided as an alcohol solution.

A zinc chloride solution was prepared by adding 0.0016 lbs. zinc chloride to deionized water to a total volume of about 0.5 gallons and mixing until the solution was clear. The heat generated from the mixing process was allowed to dissipate.

A remaining ingredient solution was prepared by adding 0.2822 lbs. glycerin, 0.0044 lbs. disodium EDTA, 0.0024 sodium citrate, 0.00158 lbs. citric acid, 0.0022 lbs. sodium saccharin, 0.006 lbs. sodium lauryl sulfate, and D & C yellow #10 and D & C green #3 in effective amounts to a quantity of deionized water such that the total volume of the resulting solution was about 3.5 gallons.

The remaining ingredient solution was mixed with the zinc chloride solution. The heat generated from the mixing process was allowed to dissipate.

The alcohol solution was mixed with the solution containing the zinc chloride and remaining ingredients.

The 1% hydrogen peroxide solution was then added to the solution containing the alcohol, zinc chloride and remaining ingredients and mixed for several minutes to form a stabilized mouthrinse containing hydrogen peroxide.

EXAMPLE 2

A mouthrinse having the composition as set forth below was prepared by the method as set forth in example 1.

| Component | % (weight/volume) |
| --- | --- |
| D.I. water | 93.85 |
| Glycerin | 2.822 |
| SDA38B2 | 2.388 |
| Poloxamer 407 | 0.398 |
| Sodium lauryl sulfate | 0.06 |
| Disodium EDTA | 0.044 |
| Flavors | 0.044 |
| Sodium citrate | 0.024 |
| Sodium saccharin | 0.022 |
| Zinc chloride | 0.016 |
| Hydrogen peroxide | 0.595 |
| Citric acid | 0.0158 |
| Coloring agents | Q.S. |

The pH of the mouthrinse was 3.925; the specific gravity at 25° C. was 1.0074.

EXAMPLE 3

Independent clinical studies, which included DNA probe analysis, were conducted using mouthrinses having the composition of Example 2 prepared in accordance with the method of the invention. The test results obtained from patients using the mouthrinse of the invention are presented in Tables I and II.

TABLE I

| | |
| --- | --- |
| Number of patients | 117 |
| % showing: | |
| reduced inflammation | 100 |
| reduced plaque | 100 |
| reduced bleeding | 98 |
| improved oral hygiene | 100 |
| Patient acceptance (%) | 94 |

TABLE II

| | |
| --- | --- |
| Number of patients | 20 |
| % showing: | |
| reduced inflammation | 100 |
| reduced plaque | 95 |
| reduced bleeding | 100 |
| improved oral hygiene | 100 |
| Patient acceptance (%) | 100 |

EXAMPLE 4

Mouthrinses having the composition of Example 2 prepared in accordance with the method of the invention were independently evaluated for antimicrobial efficacy at the University of Iowa Dows Institute for Dental Research. The tests involved a spectrum of microorganisms representing odontopathogens associated with different oral diseases. The mouthrinse was found to be antibacterially effective against all the test organisms. Various minimum inhibitory concentrations (MIC) of the mouthrinse were tested in each instance Even mouthrinse diluted substantially in distilled water killed the tested pathogens and/or inhibited their growth.

BRIEF DESCRIPTION OF THE DRAWINGS

Efficacy was eva us a spectrophotometer to measure the turbidity, in terms of absorbance of 660 nm wavelength light, of in vitro bacterial samples exposed to the mouthrinse of the invention. A lack of absorbance/turbidity corresponds to positive microbiocidal activity. FIGS. 4-9 illustrate the rate of killing of representative microorganisms by the mouthrinse. The logarithm of colony forming units per milliliter of test suspension (cfu/ml) is plotted versus time. A decrease in the number of colony forming units corresponds to positive microbiocidal activity. A. actinomycetemcomitans of FIG. 9 is considered to be a serious odontopathogen and may be associated with localized juvenile periodontitis.

EXAMPLE 5

Figure 1:
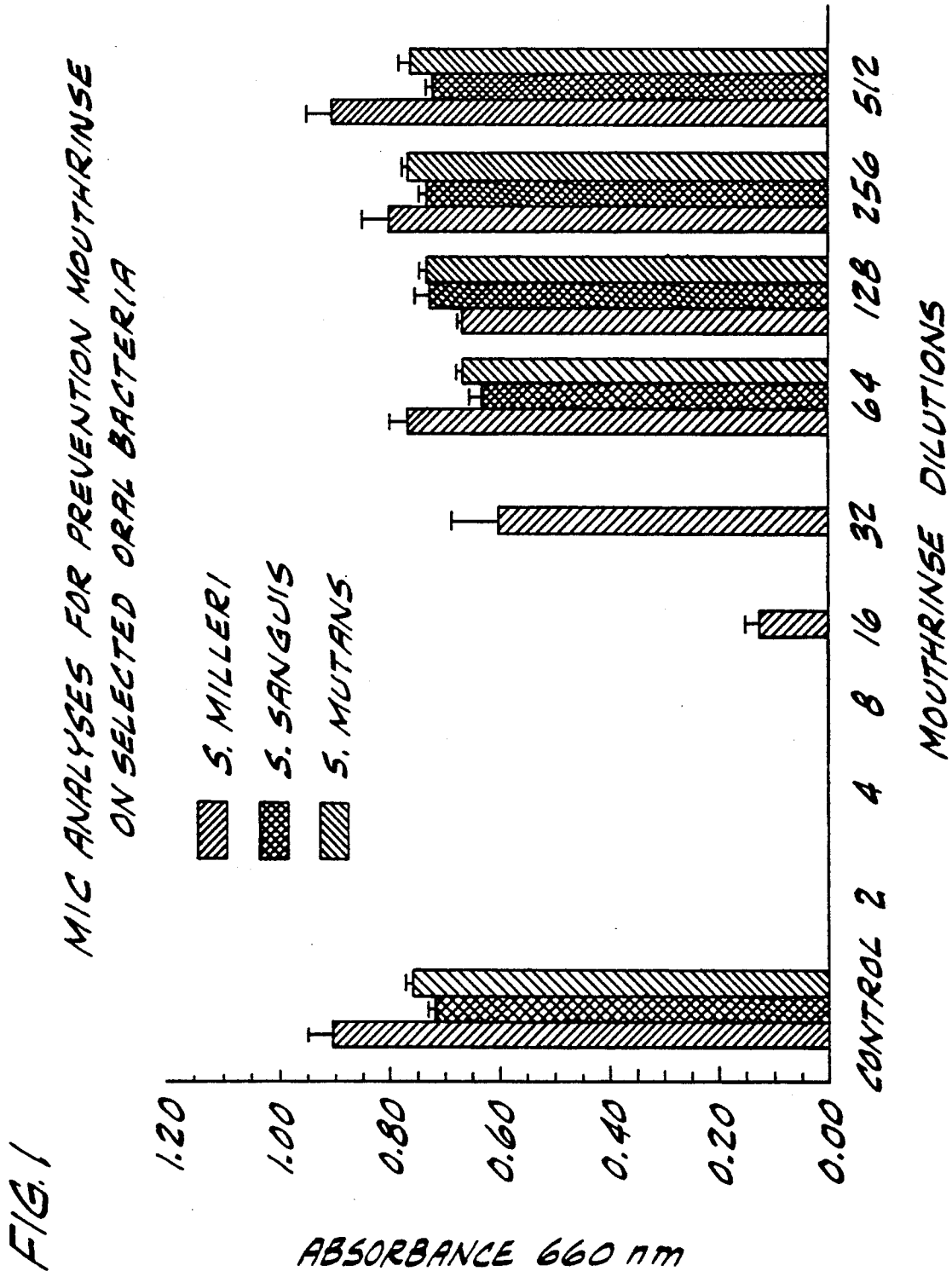
As shown in FIG. 1, three representative oral streptococci were susceptible, even with the mouthrinse diluted out to 8 and to 32 fold.
Figure 2:
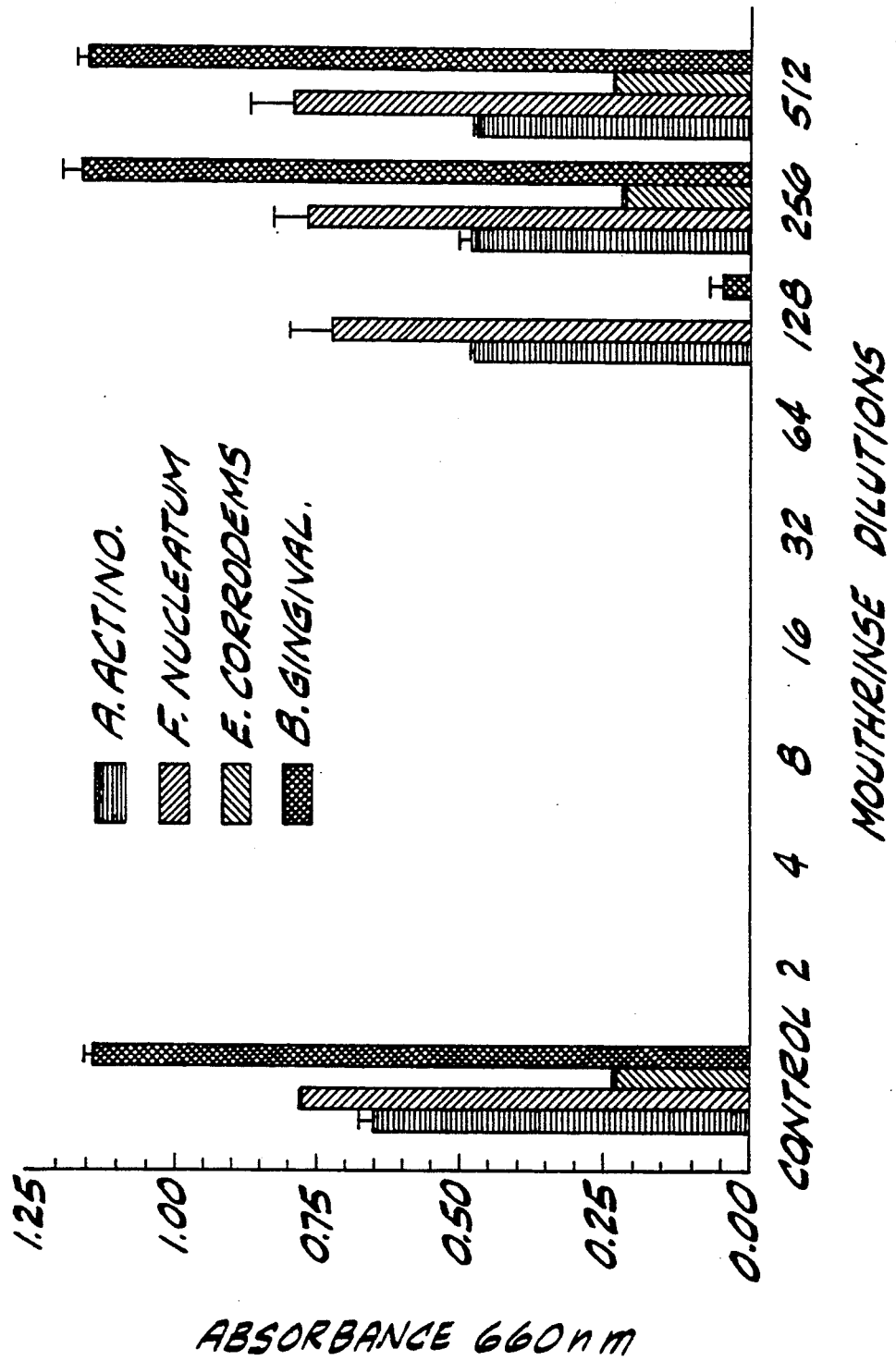
FIG. 2 illustrates the efficacy of the mouthrinse against selected periodontal pathogens
Figure 3:
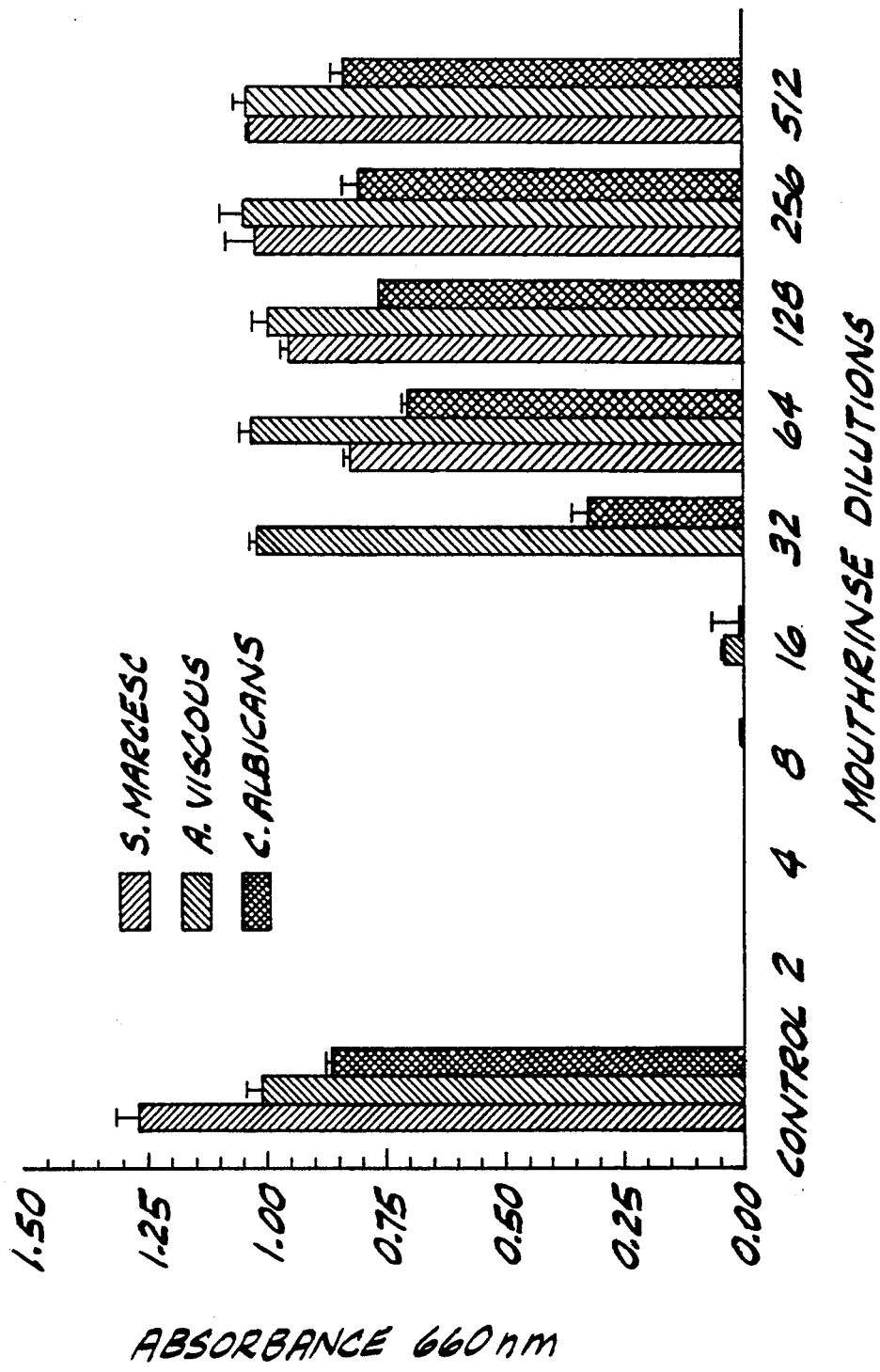
FIG. 3 illustrates the efficacy of the mouthrinse against other selected microorganisms, two of which, S. marcasens and C. albicans, may be associated with dangerous oral infections in immunocompromised patients. A. viscosus has been ass with gingivitis and root surface caries.
Figure 4:
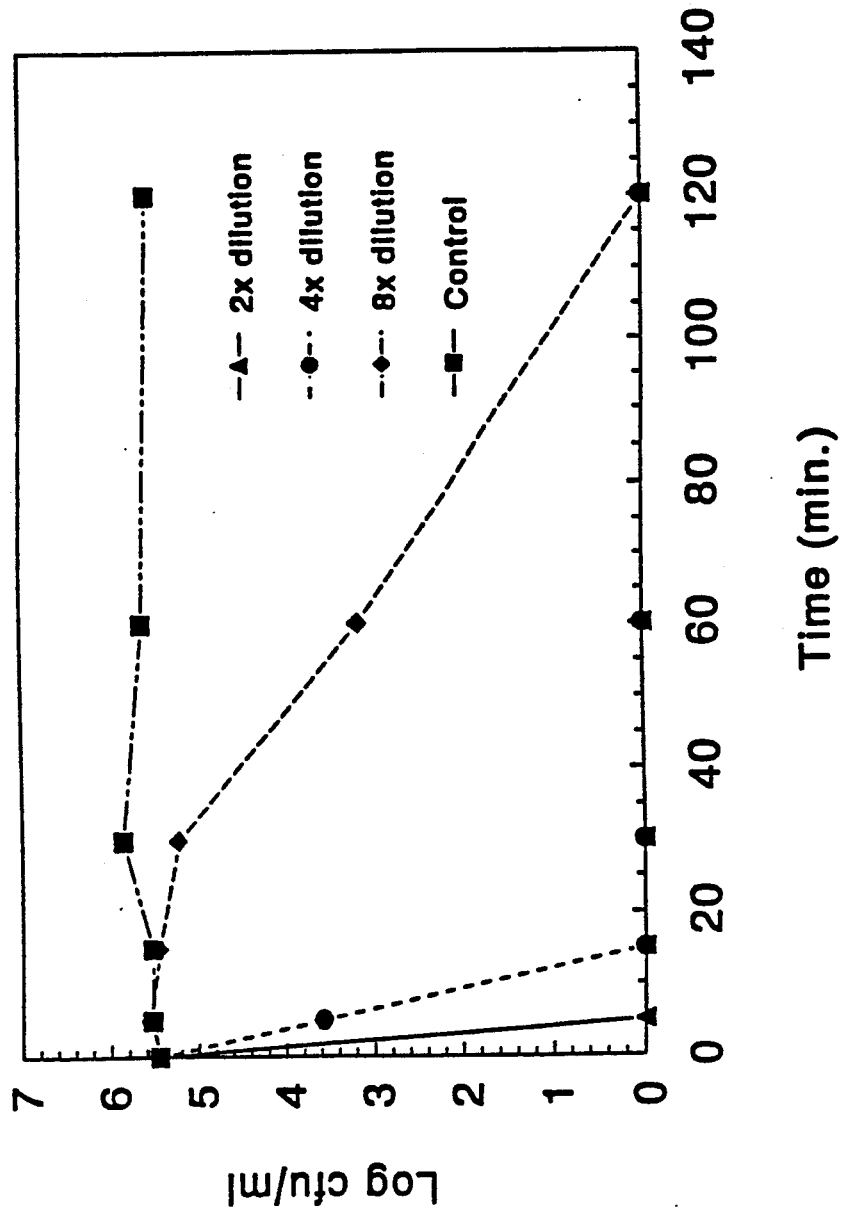
Figure 5:
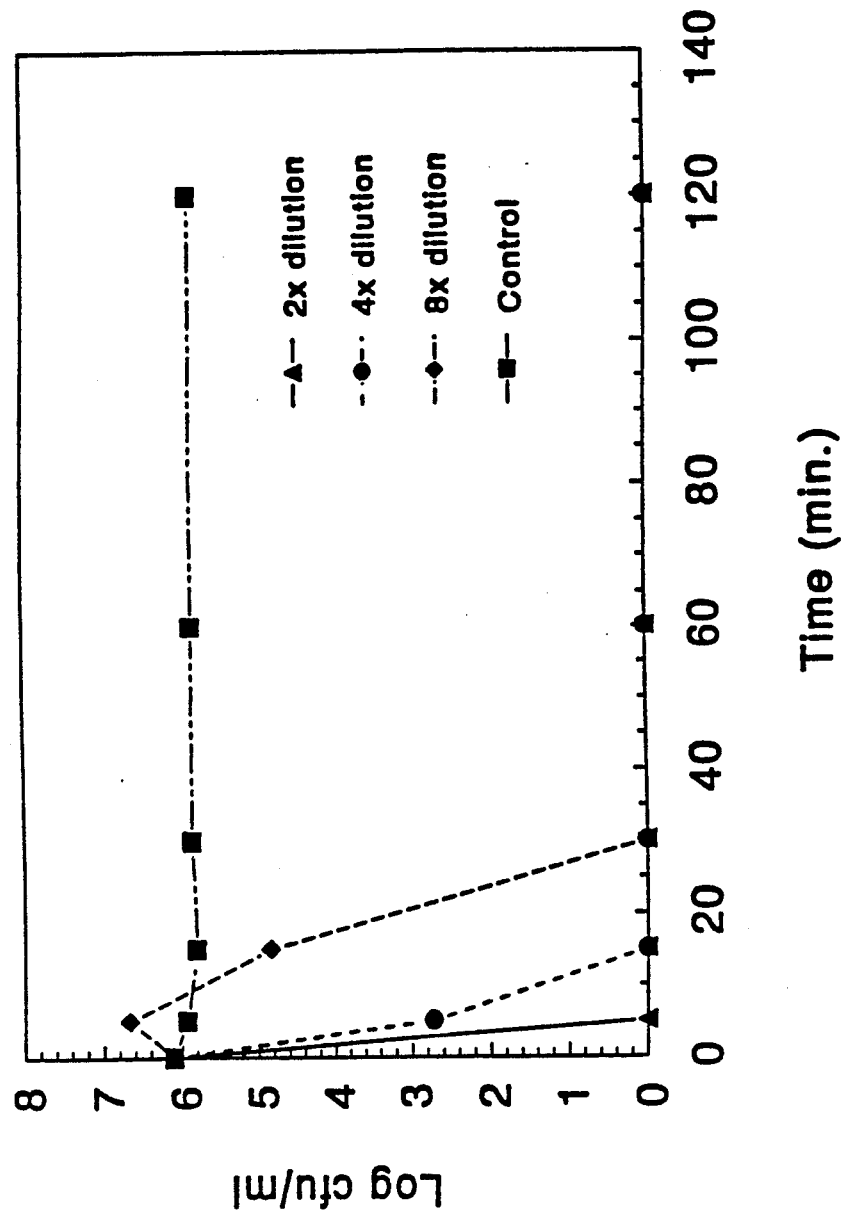
Figure 6:
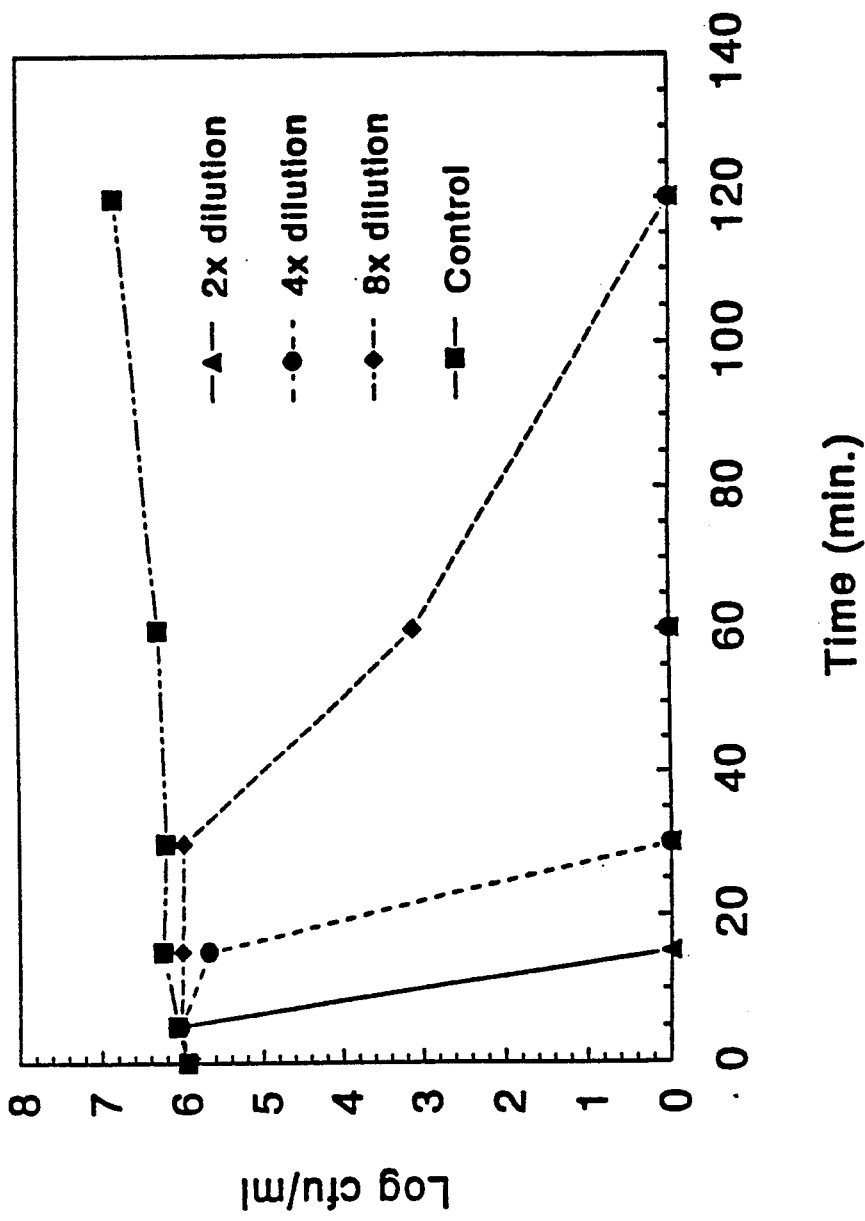

Mouthrinse having the composition of Example 2 prepared in accordance with the method of the invention was subjected to accelerated testing techniques by being held continuously at 37° C. and atmospheric pressure. After 30, 60 and 90 day intervals, the mouthrinse was stable in that the components of the mouthrinse were retained in solution with no significant evolution of gases. The mouthrinse remained clear, with no visible formation of precipitates. Under these test conditions, each thirty days of continuous exposure is estimated to correspond to one full year of shelf life.

In view of the above, it will be seen that the several objects of the invention are achieved.

Although specific examples of the present invention and its application are set forth herein, it is not intended that they are exhaustive or limiting of the invention These illustrations and explanations are intended to acquaint others skilled in the art with the invention, its principles, and its practical application, so that others skilled in the art may adapt and apply the invention in its numerous forms, as may be best suited to the requirements of a particular use.

I claim:

1. A mouthrinse preparation comprising between about 2.25% and about 0.65% hydrogen peroxide, between about 0.005% and about 0.1% zinc chloride, at least about 0.012% sodium citrate, at least about 0.03% sodium lauryl sulfate, at least about 0.006% citric acid and ethanol in an amount less than about 3%, said mouthrinse preparation having a pH such that the mouthrinse preparation remains stable upon continuous exposure to a temperature of 37° C. at atmospheric pressure for at lest 30 days.

2. A mouthrinse preparation as set forth in claim 1, said mouthrinse preparation remaining stable upon continuous exposure to a temperature of 37° C. at atmospheric pressure for at least 60 days.

3. A mouthrinse preparation as set forth in claim 1, said mouthrinse preparation remaining stable upon continuous exposure to a temperature of 37° C. at atmospheric pressure for at least 90 days.

4. A mouthrinse preparation as set forth in claim 1 wherein the sodium citrate content is such that the ratio of sodium citrate to zinc chloride is in the range of from about 1 to 1 to about 2 to 1 and ht sodium lauryl sulfate content is such that the ratio of sodium lauryl sulfate to zinc chloride is in the range of from about 2 to 1 to about 8 to 1.

5. A mouthrinse preparation as set forth in claim 1 additionally comprising a denaturing agent selected from the group of denaturing agents comprising anethole, anise oil, bay oil, bergamot oil, bitter almond oil, bubble-gum flavoring, cedar leaf oil, cinnamic aldehyde, cinnamon oil, clove oil, eucalyptol, eucalyptus oil, eugenol, lavender oil, menthol, peppermint oil, sassafras oil, spearmint oil, terpeneless spearmint oil, thyme oil, thymol and wintergreen oil.

6. A mouthrinse preparation as set forth in claim 4 additionally comprising a solubilizer.

7. A mouthrinse preparation as set forth in claim 6 wherein said solubilizer is poloxamer 407.

8. A mouthrinse preparation as set forth in claim 1 additionally comprising a surfactant.

9. A mouthrinse preparation as set forth in claim 8 wherein said surfactant is glycerin.

10. A mouthrinse preparation as set forth in claim 9 comprising between about 1.8% and about 9.0% glycerin.

11. A mouthrinse preparation as set forth in claim 1 additionally comprising a chelating agent.

12. A mouthrinse preparation as set forth in claim 11 wherein said chelating agent is disodium EDTA and constitutes between about 0.22% and about 0.1% disodium EDTA.

13. A mouthrinse preparation as set forth in claim 1 additionally comprising a coloring agent.

14. A mouthrinse preparation as set forth in claim 1 additionally comprising a sweetening agent.

15. A mouthrinse preparation consisting of between about 0.25% and about 0.65% hydrogen peroxide, between about 0.005% and about 0.1% zinc chloride, at lest about 0.012% sodium citrate, the sodium citrate content being such that the ratio of sodium citrate to zinc chloride is in the range of from about 1 to 1 to about 2 to 1, at least about 0.03% sodium lauryl sulfate, the sodium lauryl sulfate content being such that the ratio of sodium lauryl sulfate to zinc chloride is in the range of from about 2 to 1 to about 8 to 1, at least about 0.006% citric acid, ethanol in an amount less than about 3%, less than about 0.1% denaturing agent or combination of denaturing agents, between about 1.8% and about 9.0% glycerin, between about 0.022% and about 0.1% disodium EDTA, less than about 1.0% solubilizer, less than about 1.0% sweetening agent or combination of sweetening agents, and the balance of deionized water, said mouthrinse preparation having a pH such that the mouthrinse preparation has a shelf life of greater than about 2 years.

16. A mouthrinse preparation consisting essentially of between about 0.25% and about 0.65% hydrogen peroxide, between about 0.005% and about 0.1% zinc chloride, at least about 0.012% sodium citrate, the sodium citrate content being such that the ratio of sodium citrate to zinc chloride is in the range of from about 1 to 1 to about 2 to 1 on a weight percent basis, at least about 0.03% sodium lauryl sulfate, the sodium lauryl sulfate content being such that the ratio of sodium lauryl sulfate to zinc chloride is in the range of from about 2 to 1 to about 8 to 1 on a weight percent basis, at least about 0.006% citric acid, ethanol in an amount less than about 3%, less than about 0.1denaturing agent or combination of denaturing agents, between about 1.8% and about 9.0% glycerin, between about 0.022% and about 0.1% disodium EDTA, less than about 1.0% solubilizer, less than about 1.0% sweetening agent or combination of sweetening agents, and the balance of deionized water, said mouthrinse preparation having a pH such that the mouthrinse preparation has a shelf life of greater than about 2 years.

17. The mouthrinse preparation of claim 1 wherein the pH is at least about 3.5.

* * * * *